US00PP27275P3

(12) United States Plant Patent
Grosser

(10) Patent No.: US PP27,275 P3
(45) Date of Patent: Oct. 18, 2016

(54) CITRUS ROOTSTOCK NAMED 'UFR-15'

(50) Latin Name: ***Citrus grandis*×*Citrus reticulata***
Varietal Denomination: UFR-15

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,571

(22) Filed: Jan. 22, 2015

(65) Prior Publication Data

US 2015/0237781 P1 Aug. 20, 2015

Related U.S. Application Data

(60) Provisional application No. 61/942,576, filed on Feb. 20, 2014.

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

PUBLICATIONS

PLUTO: Plant Variety Database, Jan. 13, 2015, citation for 'UFR-15'. 1 page.*
U.S. Appl. No. 14/544,424, filed Jan. 5, 2015, Grosser.
U.S. Appl. No. 14/544,425, filed Jan. 5, 2015, Grosser.
U.S. Appl. No. 14/544,423, filed Jan. 5, 2015, Grosser.
U.S. Appl. No. 14/544,427, filed Jan. 5, 2015, Grosser.
U.S. Appl. No. 14/544,570, filed Jan. 22, 2015, Grosser.
U.S. Appl. No. 14/544,572, filed Jan. 22, 2015, Grosser.
U.S. Appl. No. 14/545,063, filed Mar. 20, 2015, Grosser.
U.S. Appl. No. 14/544,573, filed Jan. 22, 2015, Grosser.
Grosser et al., "Protoplast fusion and citrus improvement," *Plant Breeding Reviews* 8:339-374, 1990.
Grosser et al., "Development of "tetrazyg" rootstocks tolerant of the diaprepes/phytophthora complex under greenhouse conditions," *Proc. Fla. State Hort. Soc.* 116:263-267, 2003.
Grosser et al., "Continued Development of Rootstocks Tolerant of the *Phytophthora*-Diaprepes Complex via Greenhouse Screening," *Proc. Fla. State Hort. Soc.* 120:103-109, 2007.
Grosser et al., "Protoplast fusion for production of tetraploids and triploids: Applications for scion and rootstock breeding in citrus," *Plant Cell Tissue Organ Culture* 104:343-357, 2011.

* cited by examiner

*Primary Examiner* — Susan McCormick Ewoldt
*Assistant Examiner* — Karen Redden
(74) *Attorney, Agent, or Firm* — Dentons US LLP

(57) ABSTRACT

'UFR-15' is a new and distinct diploid hybrid *citrus* rootstock for improved disease resistance. 'UFR-15' has shown a positive reaction to the Huanglongbing disease (HLB, or *citrus* greening disease) in multiple experimental field trials. Scion trees grafted on this rootstock show a reduced frequency of infection and reduced disease symptoms once infected as compared to commercial diploid rootstocks.

6 Drawing Sheets

Latin name of the genus and species of the plant claimed: *Citrus grandis*×*Citrus reticulata*.

Variety denomination: 'UFR-15'.

BACKGROUND OF THE INVENTION

The present invention relates to a new and distinct variety of *citrus* rootstock named 'UFR-15'. The Plant Improvement Team in Lake Alfred, Fla. has pioneered the development and testing of allotetraploid *citrus* rootstocks. 'UFR-15' (identified as "46×20-04-37" in field trials) is a diploid hybrid derived from a conventional cross of Hirado Buntan pink pummelo×Cleopatra mandarin.

BRIEF SUMMARY OF THE INVENTION

'UFR-15' was selected as a potential *citrus* rootstock on the basis of its positive reaction to Huanglongbing disease (HLB, or *citrus* greening disease) in multiple experimental field trials. Scion trees grafted onto this rootstock showed a reduced frequency of infection and reduced disease symptoms once infected, when compared to other commercial diploid rootstocks. Scion trees grafted onto this rootstock grow off quickly and are vigorous in the field, producing medium-large trees comparable in size to trees on sour orange rootstock. 'UFR-15' is partially polyembryonic, and seedling populations need to be carefully rogued in nurseries to remove zygotics. 'UFR-15' is expected to grow well on calcareous soils, and should also be tolerant of blight (pummelo×mandarin hybrids in general show superior blight tolerance). Long-term performance of trees on this rootstock selection is unknown. Yield and fruit quality data is limited, and trees do not begin cropping until the 4th year (this rootstock does not induce precocious bearing). Tolerance to *Citrus tristeza* virus (CTV) is unknown, but trees grafted with CTV-infected grapefruit have shown normal growth in the greenhouse and field. True-to typeness of 'UFR-15' through asexual reproduction was demonstrated by planting a second tree of 'UFR-15' grafted to 'Swingle' citrumelo rootstock in Wimauma, Fla. Seeds from this tree and the original tree are predominantly of nucellar origin and produce true-to-type seedlings.

BRIEF DESCRIPTION OF THE DRAWINGS

'UFR-15' is illustrated by the accompanying photographs, which show the tree's form, foliage, and fruit. The colors shown are as true as can be reasonably obtained by conventional photographic procedures. The photographs are of a tree approximately 10 years old. All figures were taken in December of 2013.

DETAILED BOTANICAL DESCRIPTION

Figure 1:
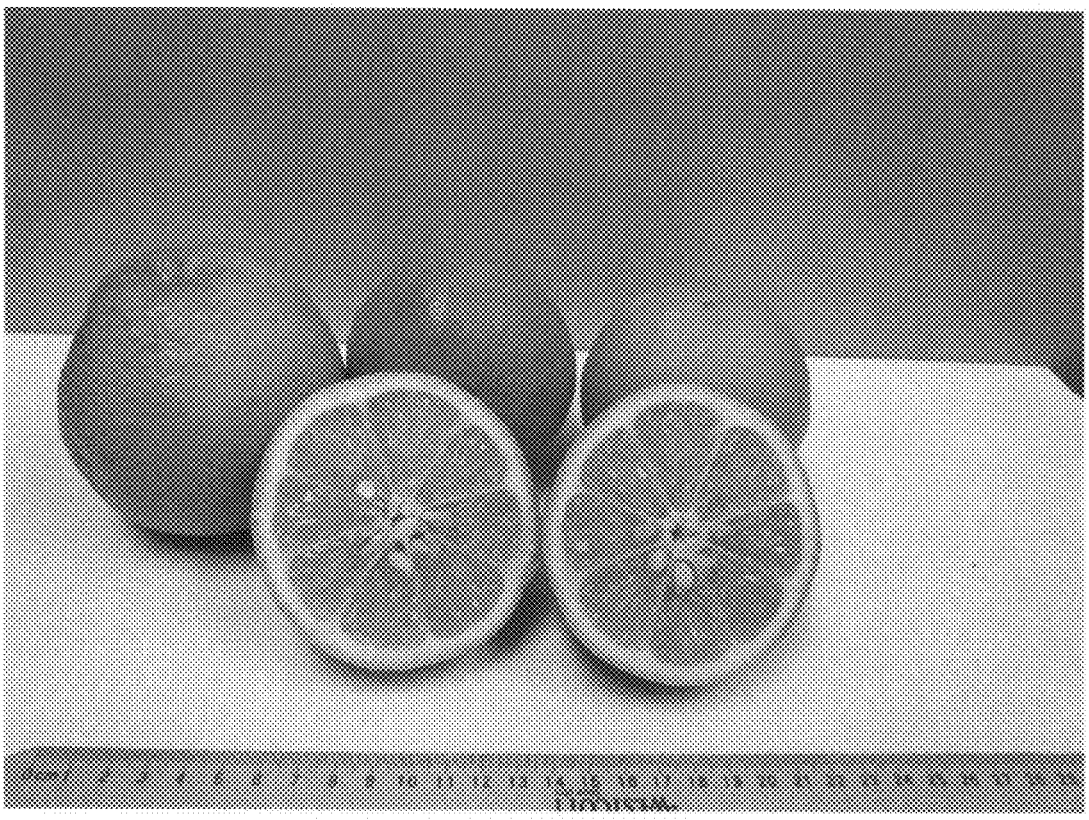
FIG. 1.—Shows a close-up of the nearly mature fruits with the rind and cross-sectional view of the fruit when cut in the center.
Figure 2:
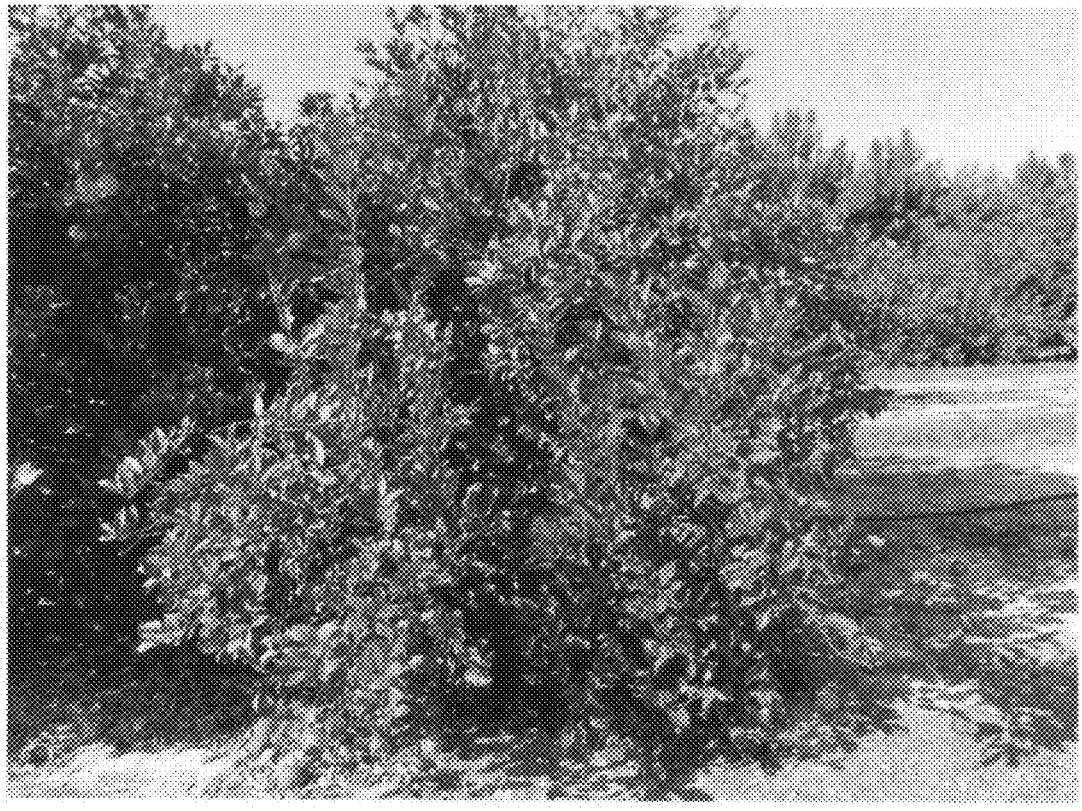
FIG. 2.—Shows the overall mature plant growth habit.
Figure 3:
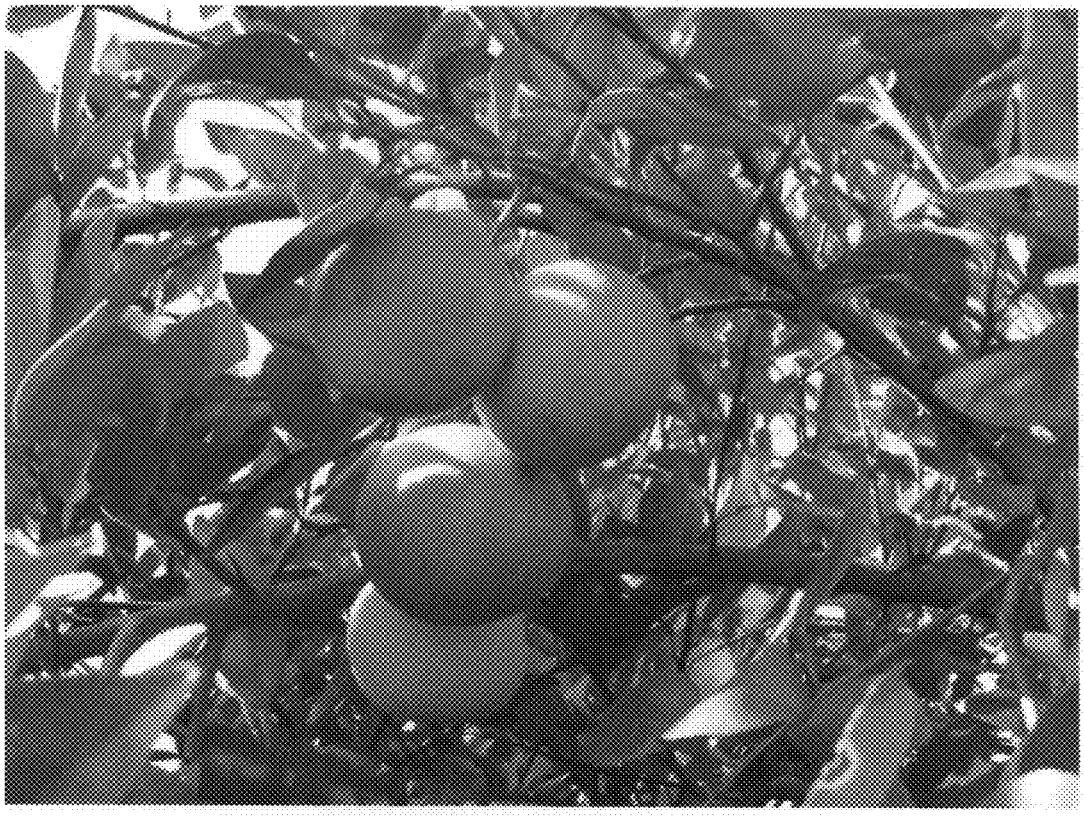
FIG. 3.—Shows mature fruits hanging on the tree.
Figure 4:
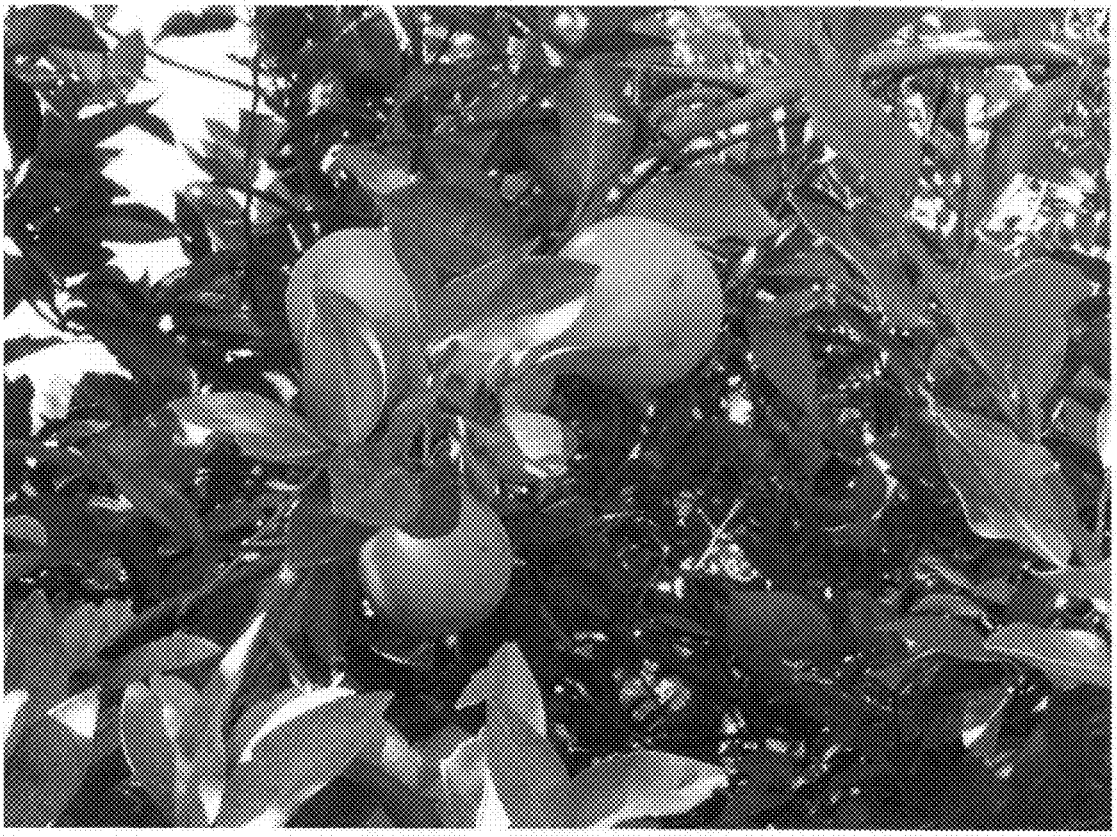
FIG. 4.—Shows leaves and mature fruits.
Figure 5:
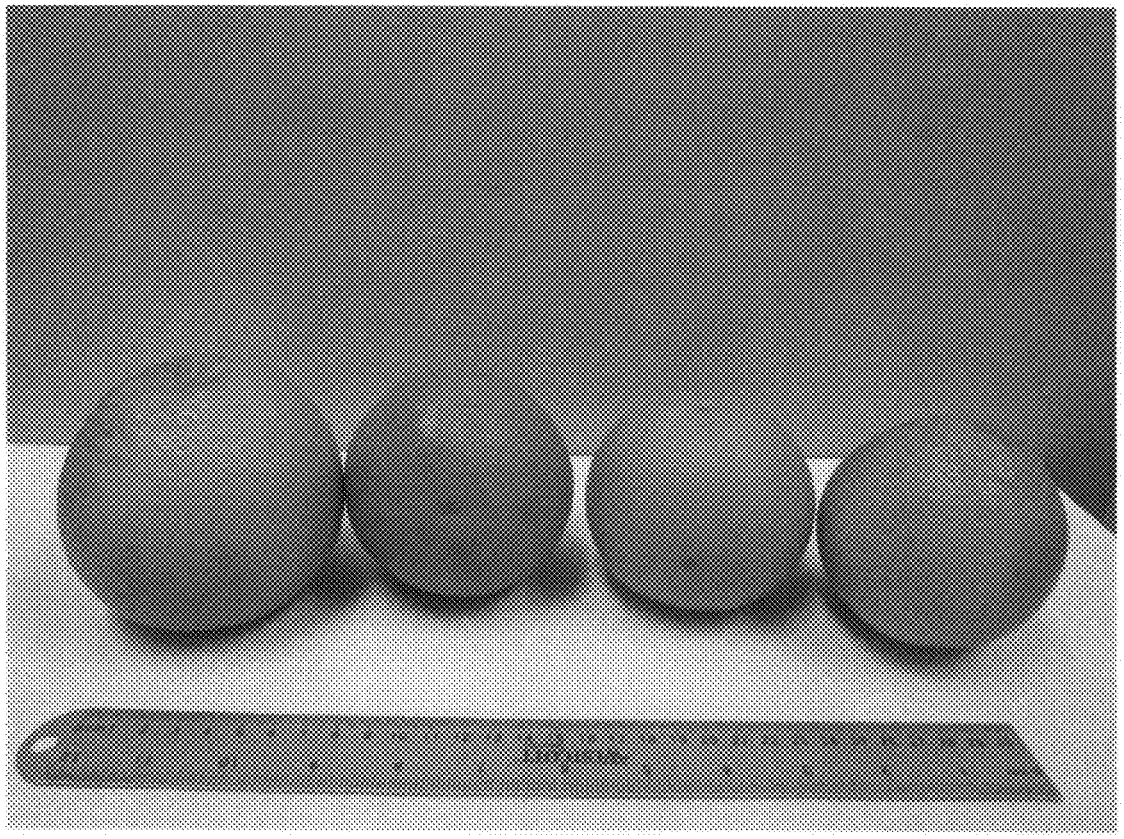
FIG. 5.—Shows a close-up of mature fruits.
Figure 6:
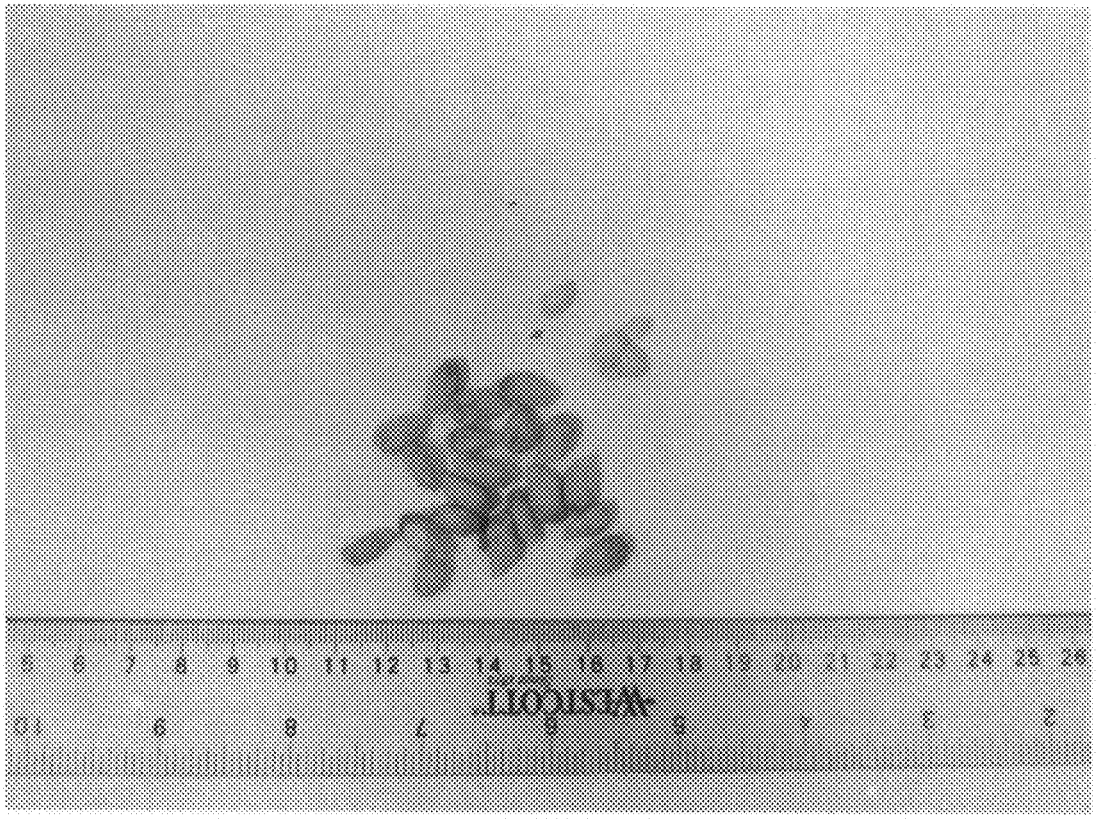
FIG. 6.—Shows a close-up of seeds from mature fruit.

The following detailed description sets forth the distinctive characteristics of 'UFR-15'. The colors (except those in common terms) are described from The R.H.S. Colour Chart published by The Royal Horticultural Society in London (second edition), in association with the Flower Council of Holland.

PHENOTYPIC DESCRIPTION OF *CITRUS GRANDIS*×*CITRUS RETICULATA* 'UFR-15'

Classification:

*Botanical.*—*Citrus grandis*×*Citrus reticulata.*

*Common name.*—Pummelo×mandarin hybrid.

Parentage:

*Female parent.*—'Hirado Buntan' pink pummelo (*Citrus grandis*, unpatented).

*Male parent.*—'Cleopatra' mandarin (*Citrus reticulata*, unpatented).

Tree:

*Ploidy.*—Diploid.

*Size.*—Medium.

*Height.*—2.45 meters.

*Tree spread.*—3.2 to 3.6 meters.

*Vigor.*—Moderately vigorous.

*Density.*—Canopies are quite dense.

*Form.*—The tree is obloid-shaped with lateral and upright branches growing. Branches with fruit exhibit drooping.

*Growth habit.*—Both upright and lateral growth with a low to medium angle.

Trunk:

*Trunk diameter.*—13.1 cm in diameter at 30 cm above the ground on a 7-year-old tree.

*Trunk texture.*—Rough.

*Trunk bark color.*—RHS 198A (greyed-green); irregularly striated with RHS 147A (yellow-green).

Branches:

*Crotch angle.*—First crotch forms 60- to 70-degree angle; middle crotch forms a 50-degree angle.

*Branch length.*—Branch reaches 3.0 meters from the first crotch to the tip of the branch.

*Branch texture.*—Relatively smooth occasionally with small thorns or spines.

*Branch color* (*shoots from previous flush, hardened and 4 to 5 mm in diameter*).—RHS N138A (green).

Leaves:

*Size* (*lamina average*).—Length: 110.8 mm. Width: 65.7 mm. L/W ratio: 1.69.

*Thickness.*—Slightly thicker than average sour orange.

*Type.*—Simple.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS N137A (green). Lower surface (abaxial): RHS 144A (yellow-green).

*Petiole.*—Shape: Brevipetiolate (shorter than leaf lamina); junction between petiole and lamina is articulate. Width (petiole wing): Narrow. Shape (petiole wing): Obovate. Length: 19.4 to 32.3 mm. Width: 5.4 to 15.2 mm. Color: RHS N137A (green).

Flowers and Flower Buds:

*Type.*—Hermaphrodite.

*Bearing.*—Flowers grow from leaf axillaries and leaf terminals singly and in small clusters; most single flowers grow from leaf axillaries. Each flower branch consists of 6-16 flowers.

*Flower diameter.*—fully open flower has an average diameter of 36.6 to 36.8 mm.

*Flower depth.*—Typical flower has an average depth of 13.6 mm.

*Flower blooming period.*—First bloom observed Mar. 16, 2014. Full bloom observed Mar. 25, 2014.

*Flower bud.*—Initial visible flower bud size: Length: 3.5 mm in length. Diameter: 1.9 mm in diameter. Mature flower bud size: Length: 15.6 mm in length. Diameter: 6.9 mm in diameter. Shape: Initial visible flower bud has a round ball shape; mature flower bud has an elongated olive shape. Color: RHS 150D (yellow-green) for initial visible flower bud; RHS 155C (white) for mature flower bud, with RHS 151D (yellow-green) spots distributed at the tip of the flower bud.

*Flower petals.*—Shape: Flat, spatula-shaped. Apex shape: Smooth, acute-shaped. Base shape: Even obtuse. Color: Upper surface RHS 155C (white); lower surface RHS 155C (white), with RHS 151D (yellow-green) spots distributed toward to the petal apex. Margin: Smooth. Length: 19.1 to 20.0 mm. Width: 7.9 to 8.1 mm. Thickness: 0.7 mm. Texture: Medium soft, smooth.

*Flower sepal.*—Number: 5 per flower. Shape: Delta-shaped with an acute angle at the apex. Length: 2.8 mm. Width: 2.0 mm. Apex shape: Most apexes appear triangle shaped, with some occasionally appearing smooth, with a round shape. Margin: Smooth. Color: Upper surface RHS 145C (yellow-green); lower surface RHS 144D (yellow-green).

*Fragrance.*—Fragrant/Moderately fragrant.

*Reproductive organs.*—Fertility: Appears self-fertile. Pollen amount: Abundant/Moderate amount. Pollen color (general): Bright-yellow. Ovary shape: Oval-shaped.

*Flower pedicel.*—Length: 5.1 to 5.2 mm. Diameter: 1.6 to 1.7 mm. Color: RHS 145C (yellow-green).

Fruit:

*Size.*—Uniform.

*Height.*—93 to 95.5 mm on average.

*Width.*—89.2 to 94.8 mm on average.

*Average weight* (*per individual fruit*).—400.8 grams.
*Shape*.—Round.
*Shape* (*cross-section*).—Round.
*Apex*.—Truncated.
*Apex cavity diameter*.—N/A.
*Base cavity diameter*.—5.8 to 7.5 mm.
*Base*.—No neck, with wrinkled shoulder.
*Harvesting*.—Fruit can be harvested from October through December in Florida.
*Fruit stem* (*short stem connecting the fruit*).—Length: 8.6 mm. Diameter: 5.7 mm. Color: RHS 189A (greyed-green) with RHS 144 (yellow-green) strip.

Rind:
*Adherence*.—Adherence between albedo (mesocarp) and flesh (endocarp) is medium. The adherence is evenly distributed from base to apex.
*Thickness*.—5.6 to 6.8 mm on average.
*Texture*.—Smooth.
*Color*.—Flavedo (epicarp): Ranges between RHS 151B (yellow-green) to RHS 151A (yellow-green). Albedo (mesocarp): RHS 150D (yellow-green).
*Stylar end*.—Closed.
*Rind oil cell density*.—185 oil cells/square cm.

Flesh:
*Number of segments*.—Between 8 and 10 segments per fruit on average.
*Segment walls*.—Medium firm with sufficient strength to maintain integrity as separated.
*Juice*.—Abundant.
*Color*.—Uniformly RHS 19B (yellow-orange).
*Texture*.—Medium/soft.
*Vesicles*.—Length: Arranged from 16 to 21 mm on average. Diameter (thickness): 3.8 to 4.2 mm on average.
*Eating quality*.—N/A.
*Juice index*.—Soluble solids (average): 7.9 Brix.

Seeds:
*Type*.—Partially polyembryonic.
*Number*.—Ranges from 20 to 23. Occasionally, some fruit contains less than 20 seeds.
*Shape*.—Seed shapes are not uniform. Normal seeds are mostly ventricose/swollen-shaped and clavate club shaped.
*Size*.—Length: 12.5 to 13 mm. Width: 5.7 to 7.5 mm.
*Seed coat color*.—Outer Surface: RHS N155B (white) and smooth/wrinkled. Inner surface: RHS 164A (greyed-orange). Cotyledon color: RHS 155A (white).

Resistance to disease: 'UFR-15' rootstock was selected on the basis of its positive reaction to HLB disease (huanglongbing or *citrus* greening disease) in multiple field trials. Trees on this rootstock show a reduced frequency of infection and reduced disease symptoms once infected as compared to commercial diploid rootstocks.

What is claimed is:

1. A new and distinct *citrus* rootstock cultivar as illustrated and described herein.

* * * * *